United States Patent [19]
Franz et al.

[11] Patent Number: 5,928,994
[45] Date of Patent: Jul. 27, 1999

[54] SYNERGISTIC HERBICIDAL COMBINATION

[75] Inventors: Richard L. Franz, Pt. Richmond, Calif.; Jee Mok Fua, Hong Kong, China; Khosro Khodayari, Walnut Creek, Calif.

[73] Assignee: Zeneca Limited, London, United Kingdom

[21] Appl. No.: 09/145,726

[22] Filed: Sep. 2, 1998

Related U.S. Application Data

[60] Provisional application No. 60/093,040, Sep. 3, 1997.

[51] Int. Cl.$^6$ .......................... A01N 31/14; A01N 43/06; A01N 43/46
[52] U.S. Cl. .......................... 504/118; 504/129; 504/220; 504/352
[58] Field of Search ..................................... 504/118, 129, 504/220, 352

[56] References Cited

U.S. PATENT DOCUMENTS 3,671,216   6/1972   Kado et al. ............... 71/100

FOREIGN PATENT DOCUMENTS

| 0 024 841 | 3/1981 | European Pat. Off. . |
| 48040931 | 6/1973 | Japan . |
| 51128431 | 11/1976 | Japan . |
| 56-032404 | 4/1981 | Japan . |
| 58-079908 | 5/1983 | Japan . |
| 59-016807 | 1/1984 | Japan . |
| 6901241 | 2/1970 | South Africa . |

OTHER PUBLICATIONS

Proceedings—Southern Weed Science Society—Challenges In Food Production—38$^{th}$ Annual Mtg.,—Jan. 1985, Houston, Tx., p. 33, Khodayari et al., *"Performance of Fenoxaprop–Ethyl and Selected Herbicides for Weed Control In Dry–Seeded Rice"*.

IRRI Annual Report for 1978, The International Rice Research Institute, 1979, Los Banos, Laguna, Philippines, pp. 201–217, *"Control and Management of Rice Pests"*.

Agrochem Japan, 1994 (No.64), pp. 4–6, Takafumi Takeshita, *"Labor Saving Granular or Flowable Herbicides for Paddy Rice Fields"*.

*Primary Examiner*—Allen J. Robinson
*Attorney, Agent, or Firm*—Dianne Burkhard

[57] ABSTRACT

Control of weeds in a rice crop is obtained by applying to the crop, the weeds, or the locus of either, a herbicidal composition containing molinate and oxyfluorfen in a weight ratio of from about 500:1 to about 30:1.

14 Claims, No Drawings

SYNERGISTIC HERBICIDAL COMBINATION

This application claims the benefit of U.S. Provisional application Ser. No. 60/093,040, filed Sep. 3, 1997.

BACKGROUND AND PRIOR ART

This invention pertains to synergistic herbicidal combinations, particularly such combinations for use in controlling weeds in a rice crop.

Molinate (S-ethyl hexahydro-1H-azepine-1-carbothioate) is a thiocarbamate herbicide which has been used to control weeds in rice crops for a number of years, and is generally sold under products bearing the trademark ORDRAM®. In different formulations and strengths, molinate is applied pre-plant, pre-flood or post-flood to control a wide range of weeds in rice crops, and is generally applied at rates ranging from about 500 to about 11,000 g/ha. However, as with many pesticides, it would be desirable to be able to achieve weed control while using a lower application rate of molinate. This could also result in less impact upon the environment and/or upon workers handling the product.

It has now been found that, surprisingly, combining of a much lower amount of the herbicide oxyfluorfen with molinate can produce a synergistic effect such that equivalent weed control can be obtained with a lesser amount and/or application rate of molinate.

Oxyfluorfen or 2-chloro-1-(3-ethoxy-4-nitrophenoxy)-4-(trifluoromethylbenzene) is a diphenyl ether herbicide sold primarily under the trademark GOAL®). Primarily, oxyfluorfen is sold for control of weeds in fruit, nut and vegetable crops, and in cotton. It is not usually used for control of weeds in rice crops because the rate of application needed to control weeds tends to cause unacceptable damage to the rice. Oxyfluorfen is used, however, in China on a small scale to control weeds in rice. In accordance with the present invention, however, the use of oxyfluorfen in an amount which produces substantially no phytotoxicity to a rice crop, in combination with molinate, particularly a lesser amount or lower application rate of molinate than is normally used, produces a synergistic effect, resulting in good control of weeds in rice crops in either pre-flood or post-flood applications.

SUMMARY OF THE INVENTION

This invention comprises a herbicidal composition as well as a method of controlling weeds in rice crops.

In one aspect, this invention relates to a synergistic herbicidal composition comprising molinate and oxyfluorfen.

In a second aspect, it comprises a herbicidal composition comprising molinate and oxyfluorfen in a weight ratio of from about 500:1 to about 30:1, respectively.

In another aspect, this invention comprises a method of controlling weeds in a rice crop comprising applying to said crop, said weeds or the locus of either or both, a synergistic combination comprising molinate and oxyfluorfen, preferably in a weight ratio of from about 500:1 to about 30:1, respectively.

DETAILED DESCRIPTION OF THE INVENTION

The invention involves the use of the combination of the herbicides molinate and oxyfluorfen to control weeds in a rice crop. The combination, within the scope of this invention, demonstrates synergistic effects, that is effects that would have been unexpected from the performance of the two herbicides individually against the same weeds under similar circumstances.

According to the invention, weeds are controlled in the presence of a rice crop by treating the crop, the weeds, or the locus of either or both, with a herbicidally effective amount of a synergistic combination of the herbicides molinate and oxyfluorfen. In general, we have found that synergy is demonstrated when the combination includes these two herbicides, respectively, in a weight ratio of from about 500:1 to about 30:1, preferably, from about 250:1 to about 40:1. However, Applicants' discovery is that of synergism between molinate and oxyfluorfen, and is not necessarily limited to combinations of these herbicides within these weight ratios, as synergy may exist at others.

This combination produces synergistic or unexpected control of weeds in rice when applied at the various times, and to rice planted in different ways. To control the weeds, the combination may be applied prior to planting, after planting but prior to flooding (pre-flood, post-emergence) or after emergence of the rice and flooding (post-flood, post-emergence) and may be applied to either direct seeded or transplanted rice.

To be used in combination, it is not necessary that the two herbicides, molinate and oxyfluorfen, be applied in a physically combined form, or even at the same time. The combination effect results so long as the two herbicides are present at the same time in the rice crop, regardless of when they were applied. Thus, for instance, a physical combination of the two herbicides could be applied, or one could be applied earlier than the other. For instance, one of the two herbicides could be applied even prior to planting the rice in a controlled release formulation such as a microencapsulated formulation, and the other applied subsequently in a conventional liquid or solid formulation, so long as the earlier-applied herbicide is still present in the soil when the second is applied, and so long as the weight ratio of available herbicides falls within that disclosed and claimed herein.

Either herbicide could thus be applied in liquid or solid form, or a combination product containing both herbicides could be produced, again, in either liquid or solid form. Typical liquid formulations include emulsions, suspensions (including suspensions containing microcapsules), solutions, emulsifiable concentrates, and flowables. Solid products include forms such as granules, wettable powders, water-dispersible solid products (including water-dispersible granules containing microencapsulated pesticides) or dusts. Both types of compositions will generally contain, in addition to the active herbicide, other ingredients such as solvents, wetting agents, suspending agents, anti-caking agents, dispersing agents, emulsifiers, antifreeze agents, antifoam agents, and other additives.

Either herbicide, or both, may be utilized in one of a number of known forms of controlled release compositions. Such compositions provide relatively slow or controlled release of the active ingredient into the environment and include, for example, encapsulations, microencapsulations, and various forms of controlled release granules.

Combination products or compositions according to this invention may contain the two herbicides in numerous different physical forms. In some cases, a combination product may be produced by simply physically mixing ("tank-mixing") commercially available products containing the active herbicides, for example, two emulsifiable concentrates containing the herbicides, so long as all the ingredients of the two products are relatively compatible. Alternatively, a package may be manufactured and sold which contains, overall, the two herbicides in separate containers, but packaged together, commonly termed a "twin-pack". A twin-pack is particularly suitable for the herbicidal compositions herein, since the amount of molinate is substantially greater than that of oxyfluorfen, so that an overall product package can be produced containing a relatively large container of a molinate-containing herbicide product together with a relatively small container of an oxyfluorfen-containing herbicidal product.

Alternatively, previously prepared compositions ("premixes") containing the two herbicides can be produced. Molinate is a liquid and oxyfluorfen in a solid which is soluble in many organic solvents. For that reason, liquid compositions appear preferable for products containing the two herbicides. Typical liquid compositions would include an emulsifiable concentrate containing both herbicides, or a two-phase emulsion (or microemulsion) with one herbicide in each phase.

However, in practice, both herbicides are currently also sold as solid formulations, that is, impregnated granules, so that a similar solid product containing both herbicides could likewise be produced, as impregnated granules. Similarly, other solid formulations such as wettable powders or dusts could be prepared.

Again similarly, using appropriate ingredients and conditions, it would be possible to prepare microencapsulated products in which one or both herbicides are contained within a microcapsule and said microencapsulated products could be sold in either liquid form (i.e., capsule suspensions) or solid form (i.e., water-dispersible granules produced by drying of microcapsule suspensions). One type of liquid form would be a microcapsule suspension in which one of the herbicides is contained within the capsules while the other is present in a nonencapsulated form, in the continuous liquid phase. Another type would be a suspension containing molinate and oxyfluorfen separately encapsulated. The types of formulations or compositions which may contain these two herbicides is not limited by those enumerated herein, as other types of formulations would likely be envisaged by those skilled in the art.

The control of weeds by the combination of oxyfluorfen and molinate is illustrated by the following example:

EXAMPLE 1

This example demonstrates application of the combination of molinate and oxyfluorfen for weed control applied post-flood/postemergence in transplanted rice. Rice was grown to the 2–4 leaf stage away separately from the trial tubs. The soil in the tub was flooded and tilled (puddled) until a blend was achieved. The rice plants were then transplanted into this blend. Weeds (2 leaf stage) were either grown separately and transplanted in or were grown in the tub on the blended soil. Herbicide application typically was made by injection or broadcasting of chemical after flooding. Combinations of molinate and oxyfluorfen in the indicated amounts were applied in the greenhouse at the application rates shown (in terms of grams per hectare of the herbicide or herbicides) to flats containing rice (Koshikari variety) and the weeds barnyardgrass (?) (*Echinochloa crusgalli*, ECHCG), smallflower flatsedge (*Cyperus difformis*, CYPDI), and monochoria (*Monochoria vaginalis*, MOOVA) at the post-flood postemergence stage. At the time of application the rice was in the 3-leaf stage, the barnyardgrass was in the 2-leaf stage and the other two weeds were intermediate the 2- and 3-leaf stages. Results of these tests are shown in Table 1, below, in terms of percent control or injury as compared to an untreated check flat.

TABLE 1

| Compound(s) | Rate, molinate g/ha | Rate, oxyfluorfen g/ha | Injury % Rice, 7 days | Rice, 28 days | % Control ECHCG | MOOVA | CYPDI |
|---|---|---|---|---|---|---|---|
| molinate | 726 | | 0 | 0 | 1 | 4 | 0 |
| | 969 | | 0 | 0 | 69 | 4 | 29 |
| | 1453 | | 1 | 0 | 51 | 0 | 38 |
| oxyfluorfen | | 3 | 1 | 0 | 0 | 24 | 8 |
| | | 6 | 1 | 0 | 0 | 35 | 14 |
| | | 13 | 0 | 0 | 35 | 38 | 23 |
| | | 25 | 3 | 0 | 100 | 50 | 30 |
| molinate/oxyfluorfen | 726 | 3 | 1 | 0 | 99 | 23 | 10 |
| | 969 | 3 | 4 | 0 | 100 | 26 | 44 |
| | 1453 | 3 | 1 | 0 | 100 | 19 | 44 |
| molinate/oxyfluorfen | 726 | 6 | 3 | 0 | 100 | 34 | 30 |
| | 969 | 6 | 4 | 1 | 100 | 34 | 54 |
| | 1453 | 6 | 1 | 0 | 100 | 49 | 64 |
| molinate/oxyfluorfen | 726 | 13 | 1 | 0 | 100 | 45 | 29 |
| | 969 | 13 | 0 | 3 | 100 | 43 | 55 |
| | 1453 | 13 | 1 | 0 | 100 | 44 | 66 |
| molinate/oxyfluorfen | 726 | 25 | 5 | 0 | 100 | 63 | 55 |
| | 969 | 25 | 1 | 0 | 100 | 59 | 88 |
| | 1453 | 25 | 1 | 0 | 100 | 61 | 96 |

From the foregoing examples, the following can be noted:

1. Molinate sparyed on barnyardgrass at 726 g/ha showed no control. Yet, when only 3 g/ha oxyfluorfen (which also showed no control) was added, control was 99%. At higher application rates, molinate alone controlled barnyardgrass to some extent. Yet when only 3–6 g/ha oxyfluorfen was added, complete control was achieved.

2. Unexpected results were not obtained on monochoria, and were only obtained on smallflower flatsedge at high application rates of oxyfluorfen (25 g/ha). However, these higher rate combinations are within the scope of this invention.

3. In some tests, combinations of molinate and oxyfluorfen within the ranges described herein did not show synergy, and this is not unexpected, as synergy is normally not shown for all possible combinations of herbicides within a given range, or on all weeds.

We claim:

1. A herbicidal composition comprising synergistic herbicidally-effective amounts of molinate and oxyfluorfen in a weight ratio of from about 500:1 to about 30:1.

2. A herbicidal composition according to claim 1 in which the weight ratio is from about 250:3.25 to about 5:1.

3. A herbicidal composition according to claim 1 in which the weight ratio is from about 250:1 to about 40:1.

4. A liquid herbicidal composition according to claim 1.

5. A solid herbicidal composition according to claim 1.

6. A controlled release herbicidal composition according to claim 1.

7. A herbicidal composition according to claim 6 in which at least one of molinate and oxyfluorfen is contained in microcapsules.

8. A method of controlling weeds in the presence of a rice crop comprising applying to said crop, said weeds, or the locus of said crop and/or said weeds, a herbicidally-effective amount of a composition according to claim 1.

9. A method of controlling weeds in the presence of a rice crop comprising applying to said crop, said weeds, or the locus of said crop and/or said weeds, a herbicidally-effective amount of a composition according to claim 2.

10. A method of controlling weeds in the presence of a rice crop comprising applying to said crop, said weeds, or the locus of said crop and/or said weeds, a herbicidally-effective amount of a composition according to claim 3.

11. A method of controlling weeds in the presence of a rice crop comprising applying to said crop, said weeds, or the locus of said crop and/or said weeds, a herbicidally-effective amount of a composition according to claim 4.

12. A method of controlling weeds in the presence of a rice crop comprising applying to said crop, said weeds, or the locus of said crop and/or said weeds, a herbicidally-effective amount of a composition according to claim 5.

13. A method of controlling weeds in the presence of a rice crop comprising applying to said crop, said weeds, or the locus of said crop and/or said weeds, a herbicidally-effective amount of a composition according to claim 6.

14. A method of controlling weeds in the presence of a rice crop comprising applying to said crop, said weeds, or the locus of said crop and/or said weeds, a herbicidally-effective amount of a composition according to claim 7.

* * * * *